(12) United States Patent
Snell et al.

(10) Patent No.: US 10,145,764 B2
(45) Date of Patent: Dec. 4, 2018

(54) CONTINUOUS FLOW SAMPLING APPARATUS HAVING AN OPENING AND FIRST AND SECOND SLIDE DOORS FOR CLOSING THE OPENING

(71) Applicant: Lincoln Global, Inc., City of Industry, CA (US)

(72) Inventors: David J. Snell, Avon Lake, OH (US); Eric A. Gulliver, Cleveland, OH (US)

(73) Assignee: LINCOLN GLOBAL, INC., City of Industry, CA (US)

(*) Notice: Subject to any disclaimer, the term of this patent is extended or adjusted under 35 U.S.C. 154(b) by 114 days.

(21) Appl. No.: 15/296,203

(22) Filed: Oct. 18, 2016

(65) Prior Publication Data

US 2017/0363520 A1    Dec. 21, 2017

Related U.S. Application Data

(60) Provisional application No. 62/350,997, filed on Jun. 16, 2016.

(51) Int. Cl.
| | |
|---|---|
| *G01N 1/28* | (2006.01) |
| *G01N 1/20* | (2006.01) |
| *G01N 1/04* | (2006.01) |
| *G01N 1/18* | (2006.01) |
| *G01N 15/06* | (2006.01) |

(52) U.S. Cl.
CPC .............. *G01N 1/20* (2013.01); *G01N 1/04* (2013.01); *G01N 1/18* (2013.01); *G01N 15/0618* (2013.01); *G01N 2001/2021* (2013.01); *G01N 2001/2092* (2013.01)

(58) Field of Classification Search
CPC .......... G01N 1/20; G01N 2001/2092

USPC ....................................... 73/863.52
See application file for complete search history.

(56) References Cited

U.S. PATENT DOCUMENTS

| 5,440,941 A | 8/1995 | Kalidindi |
| 5,549,278 A | 8/1996 | Sidler |
| 6,101,886 A | 8/2000 | Brenizer et al. |
| 6,339,966 B1 | 1/2002 | Kalidindi |

(Continued)

FOREIGN PATENT DOCUMENTS

| FR | 754 680 A | 11/1933 |
| FR | 2 908 887 A1 | 5/2008 |
| WO | 2015/094652 A1 | 6/2015 |

OTHER PUBLICATIONS

Brittain, "Particle-Size Distribution II: The Problem of Sampling Powdered Solids", Pharmaceutical Physics, Jul. 2002, article can be found online: http://images.alfresco.advanstar.com/alfresco_images/pharma/2014/08/22/665dfa8f-1163-4cd4-b6b9-924afaf29967/article-24133.pdf, accessed on Jun. 29, 2016.

(Continued)

*Primary Examiner* — Walter L Lindsay, Jr.
*Assistant Examiner* — Philip Marcus T Fadul
(74) *Attorney, Agent, or Firm* — Brad C. Spencer (57) ABSTRACT

A flow-through sampling apparatus for sampling a bulk solid mixture includes a main body forming an opening. A screen is located in the opening and forms a plurality of sample zones within the main body. The apparatus further includes a first slide door that is movable above the screen so as to close one side of the opening. Further, the apparatus includes a second slide door that is movable below the screen so as to close the other side of the opening.

19 Claims, 5 Drawing Sheets

(56) References Cited

U.S. PATENT DOCUMENTS

| 9,038,488 B2 | 5/2015 | Sinclair |
| 2004/0055362 A1 | 3/2004 | Shinohara et al. |
| 2012/0048422 A1 | 3/2012 | Dagsland |
| 2013/0104674 A1 | 5/2013 | Baptista et al. |
| 2015/0086481 A1* | 3/2015 | Ganat .................... A61K 38/17 424/1.69 |

OTHER PUBLICATIONS

"Silo Hopper Maintenance Gate", Thomas Conveyor and Equipment Company, Inc., article can be found online: http://tceconveyors.com/dilute-phase-pneumatic-conveying-system-integrators/valves-and-feeders/silo-hopper-maintenance-gates-2/, accessed on Jun. 29, 2016.

"The TR100 Range of Sample Trays for Tablets, Capsules, Liquids and Powders", Colbalt Light Systems, article can be found online: https://www.cobaltlight.com/products/trs100/accessories/, accessed on Jun. 29, 2016.

International Search Report from Corresponding Application No. PCT/IB2017/000729; dated Oct. 9, 2017.

\* cited by examiner

CONTINUOUS FLOW SAMPLING APPARATUS HAVING AN OPENING AND FIRST AND SECOND SLIDE DOORS FOR CLOSING THE OPENING

CROSS-REFERENCE TO RELATED APPLICATIONS

Benefit of U.S. Provisional Patent Application Ser. No. 62/350,997, filed Jun. 16, 2016, is hereby claimed and the disclosure incorporated herein by reference.

BACKGROUND OF THE INVENTION

Field of the Invention

Embodiments of the present invention relate to devices and methods for sampling mixtures, such as mixed bulk solids, in particular granular and/or powdered mixtures.

Description of Related Art

Bulk solids in granular or powered form are mixed and blended in various industries. Examples of such industries include chemical manufacturing, food production, the production of resin compounds, explosives, fertilizers, solid welding fluxes, pharmaceuticals, and many others. Homogeneity of the solid mixture is usually desirable.

A homogeneous solid mixture is one in which the compositions of the constituents are uniform throughout the whole mixture. Optimization of mixing devices or processes can include quantitative means to evaluate the final mixed product.

BRIEF SUMMARY OF THE INVENTION

The following summary presents a simplified summary in order to provide a basic understanding of some aspects of the devices and systems discussed herein. This summary is not an extensive overview of the devices and systems discussed herein. It is not intended to identify critical elements or to delineate the scope of such devices and systems. Its sole purpose is to present some concepts in a simplified form as a prelude to the more detailed description that is presented later.

In accordance with one aspect, provided is a flow-through sampling apparatus for sampling a bulk solid mixture. The apparatus includes a main body forming an opening. A screen is located in the opening and forms a plurality of sample zones within the main body. The apparatus further includes a first slide door that is movable above the screen so as to close one side of the opening. Further, the apparatus includes a second slide door that is movable below the screen so as to close the other side of the opening.

In a certain embodiment, the opening in the flow-through sampling apparatus is substantially circular. In another embodiment, the first slide door and the second slide includes a through hole that is substantially equal in size to the opening in the apparatus. In yet another embodiment, the plurality of sample zones have substantially equal sampling size. In a further embodiment, the sample zones each have a volume of 4 cubic centimeters. In a yet further embodiment, the apparatus further includes at least one mounting structure for mounting the apparatus on a structural member in a manufacturing process. In one version of this embodiment, the mounting structure is at least one flange. In another embodiment, the first slide door and the second slide door include a handle.

In accordance with another aspect of the device, provided is a flow-through sampling apparatus for sampling a bulk solid mixture. The apparatus includes a main body forming an opening. A screen is located in the opening and forms a plurality of sample zones within the main body. The apparatus further includes a means for selectively closing the opening and capturing a plurality of samples of the bulk solid mixture in the sample zones.

In a certain embodiment, the means for selectively closing include a first slide door movable above the screen and a second slide door movable below the screen. In one version of this embodiment, the first slide door and the second slide door include a through hole substantially equal in size to the opening in the apparatus. In another version of this embodiment, the first slide door and the second slide door include a handle. In another embodiment, the plurality of sample zones have substantially equal sampling areas. In yet another embodiment, the sample zones each have a volume of 4 cubic centimeters. In a further embodiment, the apparatus includes at least one mounting structure configured to mount the apparatus on a structural member in a manufacturing process. In a version of this embodiment, the mounting structure comprises at least one flange.

In accordance with another aspect, provided is a method of sampling a bulk solid mixture. The method includes the step of providing a flow-through sampling apparatus that includes a main body forming an opening; a screen located within the opening that forms at least one sample zone within the main body; a first slide door movable above the screen for closing the opening; and a second slide door movable below the screen for closing the opening. Another step is a passing a flow of the bulk solid mixture through the opening. Another step is closing a first side of the opening and filling at least one sample zone with the bulk solid mixture. A further step is closing the other side of the opening after at least one sample zone has at least been partially filled with the bulk solid mixture.

In a certain embodiment, the method further includes the step of placing the apparatus at an exit of a hopper (or a blender or a mixer) discharging the bulk solid mixture before passing a flow of the bulk solid mixture through the opening. In one version of this embodiment, the method further includes the step of removing the apparatus from the exit after closing the other side of the opening to seal off the opening.

BRIEF DESCRIPTION OF THE DRAWINGS

Embodiments of this invention will now be described in further detail with reference to the accompanying drawings, in which.

DETAILED DESCRIPTION OF THE INVENTION

In the following description of the present invention reference is made to the accompanying drawings which form a part thereof, and in which is shown, by way of illustration, exemplary embodiments illustrating the principles of the present invention and how it may be practiced. It is to be understood that other embodiments may be utilized to practice the present invention and structural and functional changes may be made thereto without departing from the scope of the present invention.

Embodiments of the present invention relate to a flow-through sampling apparatus. The present invention will now be described with reference to the drawings, wherein like reference numerals are used to refer to like elements throughout. It is to be appreciated that the various drawings are not necessarily drawn to scale from one figure to another nor inside a given figure, and in particular that the size of the components are arbitrarily drawn for facilitating the understanding of the drawings. In the following description, for purposes of explanation, numerous specific details are set forth in order to provide a thorough understanding of the present invention. It may be evident, however, that the present invention can be practiced without these specific details. Additionally, other embodiments of the invention are possible and the invention is capable of being practiced and carried out in ways other than as described. The terminology and phraseology used in describing the invention is employed for the purpose of promoting an understanding of the invention and should not be taken as limiting.

In reference to the disclosure herein, for purposes of convenience and clarity only, directional terms, such as, top, bottom, left, right, up, down, upper, lower, over, above, below, beneath, rear, and front, may be used. Such directional terms should not be construed to limit the scope of the invention in any manner. It is to be understood that embodiments presented herein are by way of example and not by way of limitation. The intent of the following detailed description, although discussing exemplary embodiments, is to be construed to cover all modifications, alternatives, and equivalents of the embodiments as may fall within the spirit and scope of the invention.

Disclosed is a device for capturing a cross-sectional sample of a flow stream of a bulk solid mixture in granular and/or powered form, a dry mix, or even liquids, suspensions, etc. For ease of explanation, the device will be described in the context of bulk solid mixing and sampling; however, it is to be appreciated that the device can be applied to a variety of mixing processes involving solids and/or liquids.

During the mixing process it can be important to achieve and maintain homogeneity of the mixture. The disclosed device can be placed in a flow stream and allows a cross-sectional "snap shot" of the flow stream to be sampled. The bulk solid mixture is passed through an opening in the device. One side of the opening can be closed and the bulk solid mixture can collect in the device. Then another side of the opening can be closed so that opening is sealed and a cross-sectional "snap shot" of the flow stream is sealed in the opening. A user can then test the "snap shot," and by extension the flow line, for composition and homogeneity. The user can then adjust the mixture process for the bulk solid mixture based on the test. Further, the device can segregate various portions of the cross section at different locations in the cross-sectional "snap shot", so that the composition of the one portion of the "snap shot" can be compared to the composition of another portion of the same "snap shot."

Figure 1:
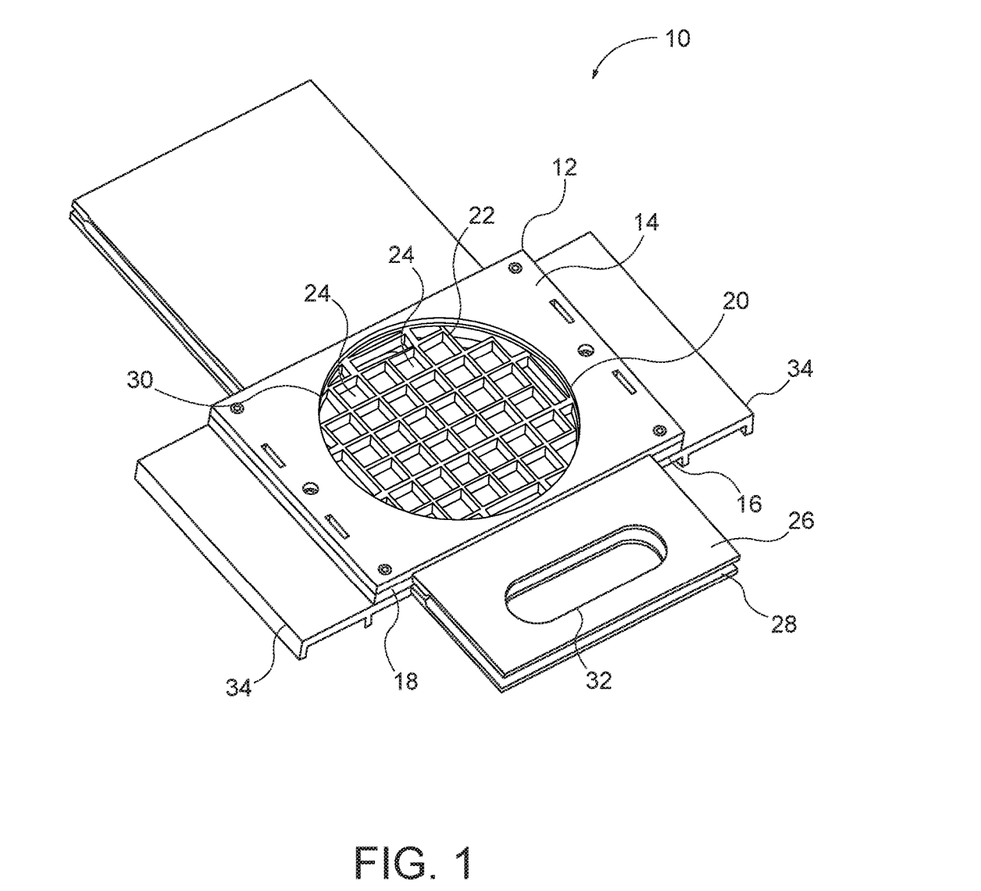
FIG. 1 shows a flow-through sampling apparatus in an open state.

Turning to FIG. 1, illustrated is one embodiment of a flow-through sampling apparatus 10. The sampling apparatus 10 comprises a main body 12. The main body 12 may have a top 14, a bottom 16, and at least one side 18. In an embodiment, shown in FIG. 1, the top 14 and bottom 16 are substantially square in shape and the side 18 comprises a front, a back, a first side, and a second side. The main body 12 may be any shape consistent with the intended use.

The main body 12 includes at least one through hole or opening 20. The main body opening 20 can extend from the top 14 to the bottom 16, from the top 14 of the main body 12 to the side 18 of the main body 12, from the bottom 16 of the main body 12 to the side 18 of the main body 12, or any orientation consistent with the intended use. For example, in FIG. 1, the main body 12 includes one main body opening 20 extending from the top 14 to the bottom 16. FIG. 1 illustrates a centrally placed main body opening 20 with respect to the main body; however other placements of the main body opening 20 with relation to the main body may be used.

The main body opening 20 can further include a screen 22. In one embodiment shown in FIG. 1, the screen 22 forms a plurality of sample zones 24 within the opening 20. The sample zones 24 can have different sizes from each other; however, it may be desirable for the screen 22 to form a plurality of sample zones 24 having substantially the same size and volume. The sample zones 24 can be substantially square in shape but can also be any shape consistent with the intended use, such as a circle, rectangle, oval, or the like. The walls of the screen 22 that separate and define the sample zones can be constructed of any material consistent with the intended use. In one embodiment, the walls separating the sample zones comprise solid walls. In other embodiments the walls separating the sample zones may comprise walls with slits. In a yet further embodiment, the walls separating the sample zones may comprise a fine mesh. FIG. 1 illustrates one embodiment of the sample zones 24 comprising a grid network of squares having substantially the same size. The screen 22 can extend the entire length of the main body opening 20 or a shorter distance if desired. In certain embodiments, the volume of the sample zones 24 established by the screen 22 can correspond to a standard sample size for a specific industry. The volume of the sample zones 24 can be modified for any scale of scrutiny, which is the smallest amount of material within which the quality of mixing is important. The volume of the sample zones 24 can range in size from several cubic microns to several hundreds of liters depending on the samples being collected (e.g., depending on the material being collected, its composition, its state as a solid, liquid, suspension, dry mix, etc.). For example, the sample zones 24 can be configured to each capture a 4 cubic centimeter (cc or $cm^3$) volume of a bulk solid mixture. A sample size of 4 $cm^3$ is merely exemplary, and substantially larger or smaller sampling sizes could be captured depending on the application and material to be sampled. Moreover, the sample zones 24 can have a wide variety of shapes, sizes diameters, perimeter lengths, cross-sections, volumes, and the like, depending on the type of material to be sampled, the volume of material being handled, etc.

The sampling apparatus 10 further includes means for preventing the material from passing through the main body opening. For example, in FIGS. 1-3, the means comprises a first movable slide door 26 and a second movable slide door 28. The first movable slide door 26 is located above the main body opening 20 and the second movable slide door 28 is located below the main body opening 20. The first movable slide door 26 slides above the screen 22 within the main body 12 of the sampling apparatus 10. The second movable slide door 28 slides beneath the screen 22 within the main body 12 of the sampling apparatus 10. The slide doors 26, 28 further include a through hole or opening 30. The slide door opening 30 can be substantially similar in shape and size to the main body opening 20. The slide door opening 30, however, may be any size and shape as desired.

The sampling apparatus 10 has at least two separate states: an open state and a fully closed state. In one embodiment, the sampling apparatus can further include a third separate state, a partially closed state. In the open state, solid material can pass through the main body opening 20. In the partially closed state, solid material will accumulate in the main body opening 20. In the fully closed state, solid material will be prevented from entering or leaving the main body opening 20.

Figure 2:
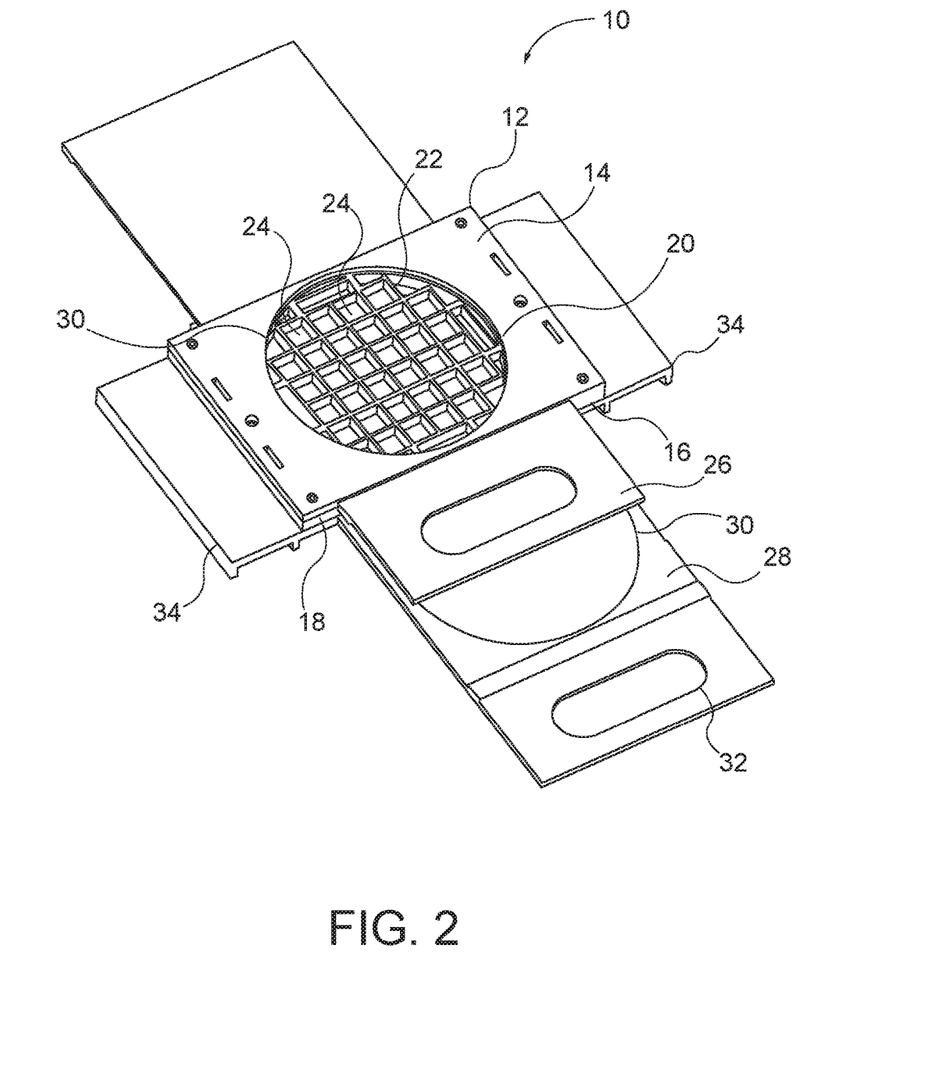
FIG. 2 shows a flow-through sampling apparatus in a partially closed state.
Figure 3:
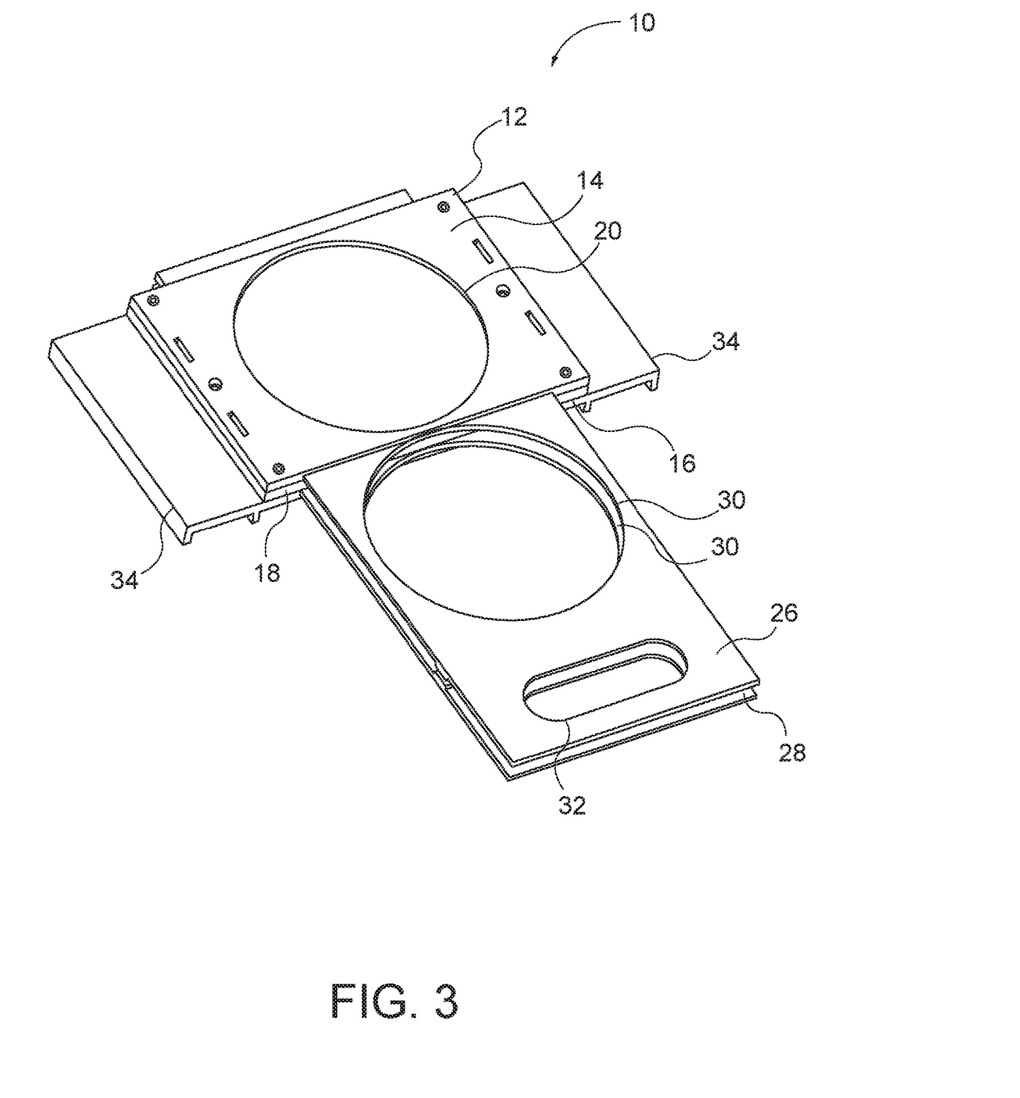
FIG. 3 shows a flow-through sampling apparatus in a fully closed state.

The slide doors 26, 28 may each have a first and second orientation. In the first orientation, the slide door opening 30 is aligned with the main body opening 20. If both slide doors 26, 28 are in the first orientation, the device is in the open state. An example of the open state for an example embodiment is illustrated in FIG. 1. In the second orientation, the slide door opening 30 is out of alignment with the main body opening 20 and the main body opening 20 is blocked by the slide door. If one slide door is in the first orientation and the other slide door is in the second orientation, the invention is in the partially closed state. In the partially closed state, solid material may enter the main body opening 20 through the slide door in the first orientation and collect in the main body opening 20. An example of the partially closed state for an example embodiment is illustrated in FIG. 2 with the first movable slide door 26 in the first orientation and the second movable slide door 28 in the second orientation. If both slide doors are in the second orientation, the invention is in a fully closed state. In the fully closed state, solid material cannot enter the main body opening 20 and solid material collected in the main body 12 before the invention entered the fully closed state will remain in the now enclosed main body opening 20. An example of the fully closed state for an example embodiment is illustrated in FIG. 3 with the first movable slide door 26 and the second movable slide door 28 in the second orientation.

In a further embodiment, the slide doors 26, 28 each include a handle 32 for manually opening and closing the slide door 26, 28. In another embodiment, the slide doors 26, 28 are operated automatically, such as by a solenoid, and the handle may be omitted.

The sampling apparatus 10 can be mounted in line within a flow stream of a bulk solid mixture, which is poured or otherwise flows through the main body opening 20. The sampling apparatus 10 can further include mounting structures 34. The mounting structures 34 can be configured for mounting in a particular manufacturing process. In FIG. 1, for example, the mounting structures 34 comprise flanges or outriggers that allow the sampling apparatus 10 to be placed onto a structural member (e.g., a framework) 36 associated with bulk mixing equipment. The sampling apparatus can be hung by the outriggers along a bulk solid mixture flow stream, so that a flow stream passes through the main body opening.

Figure 4:
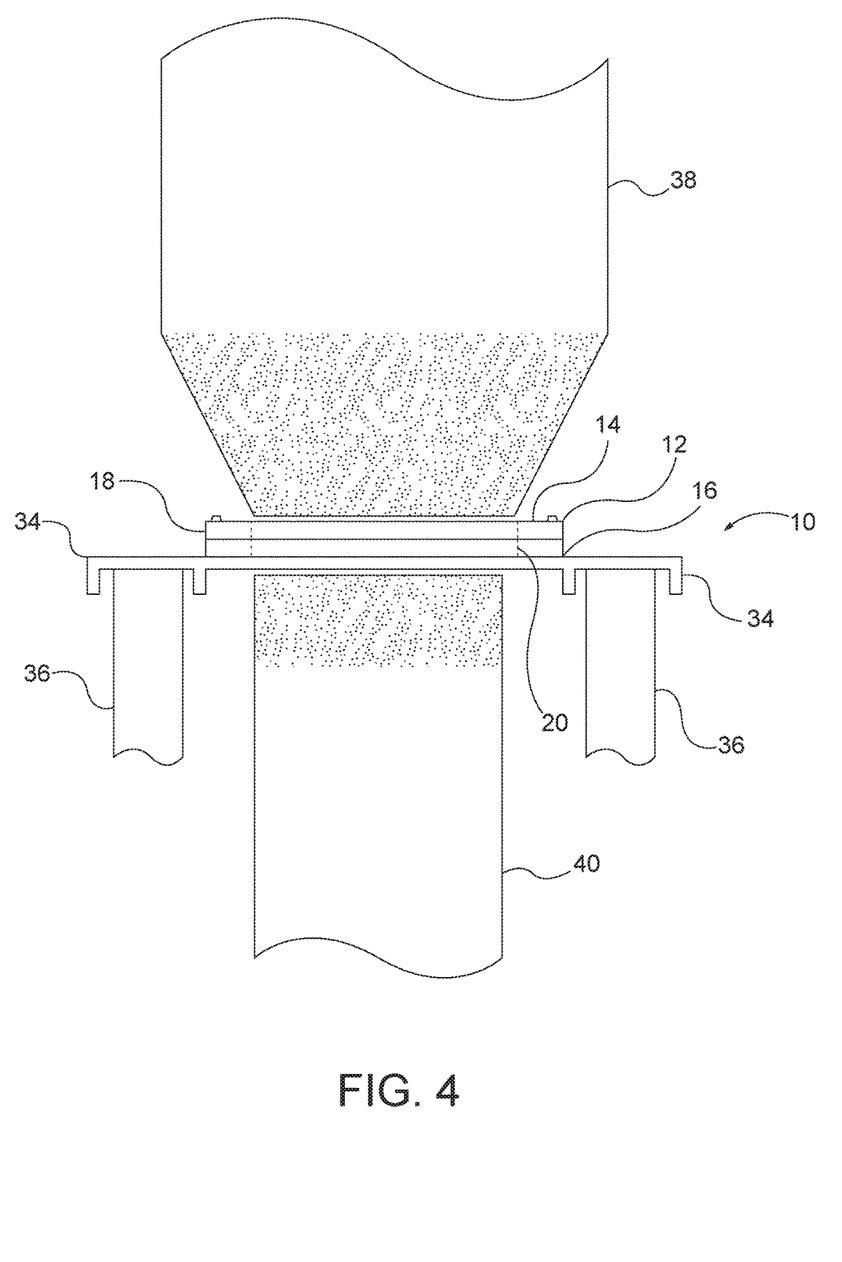
FIG. 4 shows a flow-through sampling apparatus inline in a bulk mixing process.

FIG. 4 illustrates the embodiment of the device shown in FIG. 1 mounted in line within a flow stream of a bulk solid mixture. The flow-through sampling apparatus 10 is positioned between a hopper or blender or mixer or the like 38 (hereinafter referred to as a "hopper" for simplicity) and a collection vessel 40. The flanges 34 are placed onto structural members 36 to support the sampling apparatus 10. The mixture flows from the hopper 38 through an opening 20 in the sampling apparatus 10 and further into the collection vessel 40.

FIG. 4 illustrates one embodiment of the device used in a gravity controlled flow stream. The device can be adapted to any intended flow stream type. For example, the device can be placed in the flow stream of a pressurized line that is pressurized by a gas. Pressurized air, for example, can be used to push or otherwise move the mixture through the line. In such an embodiment, the slide doors 26, 28 can comprise a mesh, web, net, or the like. The mesh is designed to prevent the mixture from passing through the open spaces in the mesh while allowing the pressurized air to pass through the open spaces. Thus, if a slide door 26, 28 is in the second state, the pressurized air will pass through the open spaces in the mesh while preventing the flux from passing through the open spaces in the mesh, thereby capturing the mixture in the sample zones.

Figure 5:
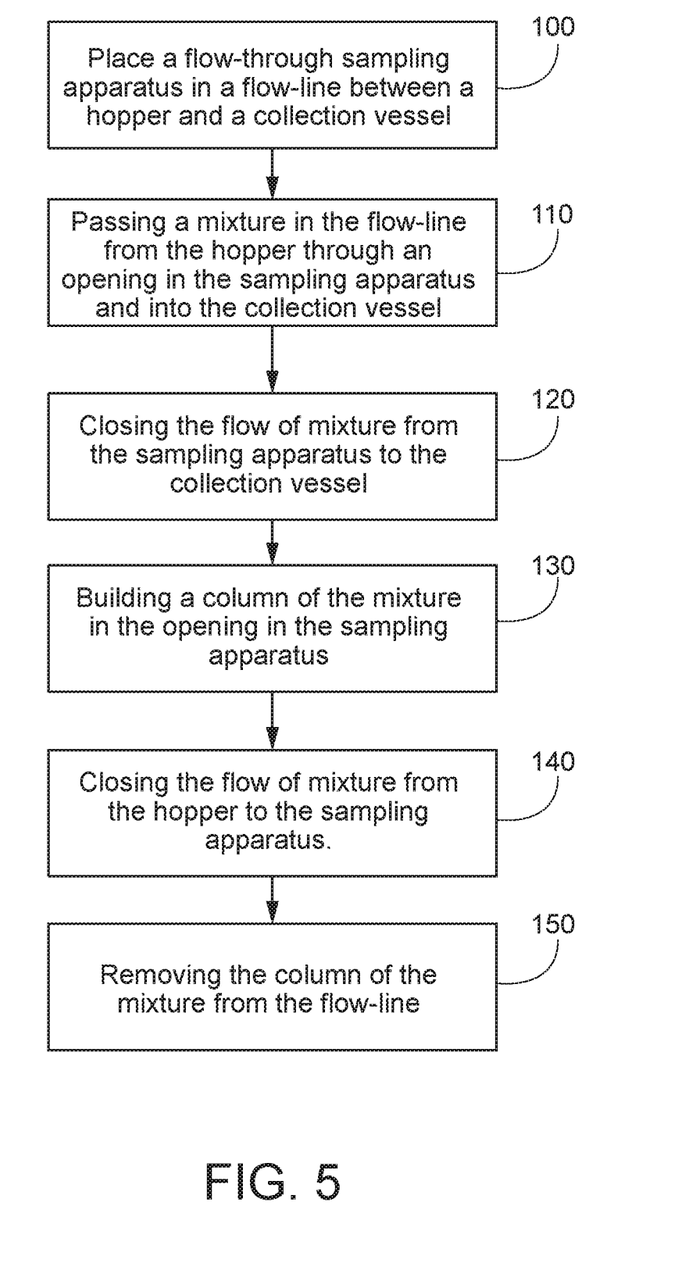
FIG. 5 shows a flow chart illustrating the operation of the flow-through sampling apparatus, according to an embodiment.

FIG. 5 is a flowchart illustrating in greater detail one embodiment of a method for collecting a cross-sectional sample of a bulk solid mixture. The method begins at block 100 in which a flow-through sampling apparatus 10 is placed in a flow-line between a hopper 38 and a collection vessel 40 where the hopper 38 is above the sampling apparatus 10 and the collection vessel 40 is below the sampling apparatus 10. Moving to block 110, the mixture flows in the flow-line from the hopper 38 through an opening 20 in a flow-through sampling apparatus 10 into the collection vessel 40. In one embodiment, the opening 20 is at least the size of an exit of the hopper 38 such that all the mixture exiting the hopper passes through the opening 20. Moving to block 120, the flow of the mixture below the opening 20 is closed off. As described above, the flow of mixture can be stopped by a movable slide door located below the opening. Moving to block 130, a columnar volume of material builds up in the opening 20. In one embodiment, the columnar volume fills the entire opening 20; in another embodiment the columnar volume partially fills the opening 20. Moving to block 140, the flow of the mixture into the opening is closed off. As described above, the flow of the mixture can be stopped by a movable slide door located above the opening. Moving to block 150, the columnar volume of material can then be removed from the flow-line.

In one embodiment, the columnar volume of material is removed from the flow-line by removing the sampling apparatus 10 from the flow-line. In a further embodiment, after the opening 20 is closed off, flow of the granular mixture from the hopper 38 is stopped. In a yet further embodiment, after the opening 20 is closed off, flow of the granular mixture from the hopper 38 is not stopped and a runoff collector (not pictured) is provided such the granular mixture can continue to flow into the collection vessel 40. In another embodiment, the columnar volume of material is removed separately from the main body 12.

A user can then test composition of the bulk solids in the columnar volume of material. The user would confirm that the composition is within at least one preset threshold limitation. If the compositions do not comply with the limitation, the flow stream can be stopped and the flow-line can be adjusted to comply with the limitation. Further, a composition of bulk solids in a columnar volume of material in a first sample zone 24 can be compared to a composition of bulk solids in a columnar volume of material in at least one other sample zone 24 of a same cross-sectional sample (e.g., to confirm homogeneity of the mixture). Optionally, a composition of bulk solids in a columnar volume of material in a sample zone 24 can be compared to prior measured composition(s) of bulk solids in a columnar volume of material for the same sample zone 24. A user can also test other characteristics of a sample, such as size of the material collected, density, or any other characteristic a user desires.

In one embodiment, at least one testing apparatus (not pictured) is attached to at least one sample zone 24. The testing apparatus can provide visual or other feedback to a user of the sampling apparatus 10, e.g., regarding the composition, homogeneity, etc., of one or more samples. To this end, the testing apparatus can be any type best suited for the sample being tested. For example, in one embodiment the testing apparatus is reactive paper that reacts to a specific chemical composition. In another embodiment, the testing apparatus includes chemicals that react in a specific manner to the presence of certain materials in a sample. In a yet further example, the testing apparatus includes a sensor to determine certain characteristics about the sample. In an embodiment in which one or more sample zones includes a sensor, the sampling apparatus can be operatively connected to local or remote test equipment for monitoring the various material characteristics discussed above.

Further embodiments of the device are also possible. For example, FIGS. 1-3 illustrate an opening in a main body 12 that is generally circular in shape. The opening 20 can also be any shape consistent with the intended use, such as a square, rectangle, oval, or the like. Further, the sampling apparatus 10 can be constructed from any suitable material, such as metal (e.g., stainless steel), polymers, ceramics, or from other suitable materials for any type bulk solid mixing. Yet further, different sections of the sampling apparatus 10 can be constructed from different material as is suitable based on different factors, such as the location or orientation of the sampling apparatus 10 or the type of material being tested.

In a yet further embodiment, receiving vessels (e.g., sample bottles—not shown) can be positioned beneath the sample zones to receive the cross-sectional samples. The sampling apparatus can be moved to the receiving vessels, or the receiving vessels can be moved beneath the sampling apparatus. When the receiving vessels are positioned beneath their corresponding sample zones 24, the second movable slide door 28 can be moved to the first orientation to release the samples into the receiving vessels. The different samples can then be analyzed for proper composition and homogeneity.

The main body 12 of the sampling apparatus 10 and/or the slide doors 26, 28 can include stops (not pictured) to limit the movement of the slide doors 26, 28 when opening and/or closing the slide doors 26, 28.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

What is claimed is:

1. A flow-through sampling apparatus for sampling a bulk solid mixture, comprising:
   a main body forming an opening aligned with both of a collection vessel and a hopper discharge that discharges a flow stream of the bulk solid mixture through the opening and through the flow-through sampling apparatus into the collection vessel;
   a screen located within the opening in the main body and forming a plurality of sample zones within the main body;
   a first slide door movable above the screen for closing the opening in the main body; and
   a second slide door movable below the screen for closing the opening in the main body thereby capturing a cross-sectional sample of the flow stream within the plurality of sample zones,
   wherein the first slide door and the second slide door include respective through holes substantially equal in size to the opening.

2. The flow-through sampling apparatus of claim 1, wherein the opening is substantially circular.

3. The flow-through sampling apparatus of claim 1, wherein the plurality of sample zones have substantially equal sampling areas.

4. The flow-through sampling apparatus of claim 1, wherein a first sample zone has a first sampling area and a second sample zone has a second sampling area, wherein the second sampling area is larger than the first sampling area.

5. The flow-through sampling apparatus of claim 1, wherein a first sample zone comprises a first cross-sectional shape and a second sample zone has a second cross-sectional shape, wherein the first cross-sectional shape is different from the second cross-sectional shape.

6. The flow-through sampling apparatus of claim 1, wherein the sample zones each have a volume of 4 cubic centimeters.

7. The flow-through sampling apparatus of claim 1, further including at least one mounting structure configured to mount the apparatus on a structural member in a manufacturing process.

8. The flow-through sampling apparatus of claim 7, wherein the mounting structure comprises outriggers that hang the flow-through sampling apparatus between the hopper discharge and the collection vessel.

9. The flow-through sampling apparatus of claim 1, wherein the first slide door and the second slide door include a handle.

10. A flow-through sampling apparatus for sampling a bulk solid mixture, comprising:
    a main body forming an opening aligned with both of a collection vessel and a hopper discharge that discharges a flow stream of the bulk solid mixture through the opening and through the flow-through sampling apparatus into the collection vessel;
    a screen located within the opening in the main body and forming a plurality of sample zones within the main body; and
    means for selectively closing the opening in the main body and capturing a cross-sectional sample of the flow stream as a plurality of samples of the bulk solid mixture in the sample zones, wherein the means for selectively closing the opening includes a through hole substantially equal in size to the opening in the main body.

11. The flow-through sampling apparatus of claim 10, wherein the opening in the main body is substantially circular.

12. The flow-through sampling apparatus of claim 10, wherein the plurality of sample zones have substantially equal sampling areas.

13. The flow-through sampling apparatus of claim 10, wherein a first sample zone has a first sampling area and a second sample zone has a second sampling area, wherein the second sampling area is larger than the first sampling area.

14. The flow-through sampling apparatus of claim 10, wherein a first sample zone comprises a first cross-sectional shape and a second sample zone has a second cross-sectional shape, wherein the first cross-sectional shape is different from the second cross-sectional shape.

15. The flow-through sampling apparatus of claim 10, wherein the sample zones each have a volume of 4 cubic centimeters.

16. The flow-through sampling apparatus of claim 10, further including at least one mounting structure configured to mount the apparatus on a structural member in a manufacturing process.

17. The flow-through sampling apparatus of claim 16, wherein the mounting structure comprises outriggers that hang the flow-through sampling apparatus between the hopper discharge and the collection vessel.

18. A method of sampling a bulk solid mixture, the method comprising the steps of:
  providing a flow-through sampling apparatus, the flow-through sampling apparatus comprising:
    a main body forming an opening;
    a screen located within the opening in the main body and forming a plurality of sample zones within the main body; and
    a first slide door movable above the screen for blocking the opening in the main body; and
    a second slide door movable below the screen for blocking the opening in the main body;
  locating the flow-through sampling apparatus between a collection vessel and a hopper discharge;
  passing a flow stream of the bulk solid mixture from the hopper discharge through the opening, through the flow-through sampling apparatus and into the collection vessel;
  blocking a first side of the opening and filling the plurality of sample zones with the bulk solid mixture thereby capturing a cross-sectional sample of the flow stream within the plurality of sample zones; and
  blocking the other side of the opening after at least one sample zone has at least been partially filled with the bulk solid mixture,
  wherein the first slide door and the second slide door include respective through holes substantially equal in size to the opening.

19. The method of claim 18, wherein the flow-through sampling apparatus includes outriggers that hang the flow-through sampling apparatus between the hopper discharge and the collection vessel.

* * * * *